United States Patent
Neergaard et al.

(10) Patent No.: US 7,365,700 B2
(45) Date of Patent: Apr. 29, 2008

(54) DEVICE FOR SHIELDING ELECTRONIC UNITS INCLUDING A TRANSMITTING/RECEIVING EQUIPMENT, AND ESPECIALLY FOR SHIELDING MOBILE PHONES

(75) Inventors: Per Jan Neergaard, Copenhagen (DK); Karsten Frank Rye Madsen, Slagelse (DK); Hannah B. Zweidorff, Dianalund (DK); René Bozzini, Via Minigera 20, CH-6926 Montagnola (CH)

(73) Assignees: Hannah Zweidorff, Dianalund (DK); Rene Bozzini, Montagnola (CH)

( * ) Notice: Subject to any disclaimer, the term of this patent is extended or adjusted under 35 U.S.C. 154(b) by 0 days.

(21) Appl. No.: 10/551,427

(22) PCT Filed: Apr. 2, 2004

(86) PCT No.: PCT/DK2004/000236
§ 371 (c)(1),
(2), (4) Date: Oct. 3, 2005

(87) PCT Pub. No.: WO2004/088789
PCT Pub. Date: Oct. 14, 2004

(65) Prior Publication Data
US 2006/0132363 A1 Jun. 22, 2006

(30) Foreign Application Priority Data
Apr. 4, 2003 (WO) .................... PCT/DK03/00219
Dec. 8, 2003 (DK) .............................. 2003 01804

(51) Int. Cl.
*H01Q 1/52* (2006.01)
*H01Q 1/24* (2006.01)
(52) U.S. Cl. ..................................... 343/841; 343/702

(58) Field of Classification Search ................ 343/702, 343/841
See application file for complete search history.

(56) References Cited

U.S. PATENT DOCUMENTS

| 4,800,395 | A | | 1/1989 | Garay et al. |
| 5,819,162 | A | * | 10/1998 | Spann et al. .............. 455/575.5 |
| 6,088,579 | A | * | 7/2000 | Sepponen ................ 455/575.5 |
| 6,163,300 | A | * | 12/2000 | Ishikawa et al. ............ 343/702 |
| 6,208,300 | B1 | * | 3/2001 | Johnson ....................... 343/702 |
| 6,246,374 | B1 | * | 6/2001 | Perrotta et al. ............. 343/702 |
| 6,285,327 | B1 | * | 9/2001 | See .............................. 343/702 |
| 6,369,765 | B1 | * | 4/2002 | Davis .......................... 343/702 |
| 6,380,895 | B1 | * | 4/2002 | Moren et al. ........ 343/700 MS |
| 6,456,249 | B1 | * | 9/2002 | Johnson et al. ............. 343/702 |

(Continued)

FOREIGN PATENT DOCUMENTS

BE      1 003 660 A       5/1992

(Continued)

*Primary Examiner*—Hoang V Nguyen
*Assistant Examiner*—Robert Karacsony
(74) *Attorney, Agent, or Firm*—Birch, Stewart, Kolasch & Birch, LLP

(57) ABSTRACT

The invention relates to a device shielding especially an electronic unit with a transmitter, such as a mobile phone, against electromagnetic radiation. The device includes a crystal and an winding/spiral, where the winding/spiral is wound with the crystal arranged in the middle. One end of the winding extends immediately adjacent the antenna of the electronic unit. The device includes also a second winding of ferromagnetic material and a metallic film.

9 Claims, 5 Drawing Sheets

U.S. PATENT DOCUMENTS

| | | |
|---|---|---|
| 2003/0011530 A1 | 1/2003 | Lin |
| 2003/0122983 A1* | 7/2003 | Kim et al. .................... 349/43 |

FOREIGN PATENT DOCUMENTS

| | | |
|---|---|---|
| DE | 33 04 155 A | 8/1984 |
| DE | 39 15 832 A | 12/1990 |
| DE | 43 17 884 A | 2/1994 |
| DE | 44 25 261 A | 1/1996 |
| EP | 0 367 609 A | 5/1990 |
| EP | 0 838 208 A | 4/1998 |
| EP | 100 51 225 A | 1/2002 |

* cited by examiner

DEVICE FOR SHIELDING ELECTRONIC UNITS INCLUDING A TRANSMITTING/RECEIVING EQUIPMENT, AND ESPECIALLY FOR SHIELDING MOBILE PHONES

TECHNICAL FIELD

The invention relates to a device for shielding an electronic unit, especially an electronic unit including a transmitter, against electromagnetic radiation.

BACKGROUND ART

A few years ago the mobile phones were both expensive and unusual, and therefore the possible detrimental effects of the mobile phones were not in focus. Today, the latter attitude has changed, among other things because the majority of the population in many countries own both an ordinary land based phone at home and a mobile phone to take with them. Therefore, the question has been raised whether or not the electromagnetic radiation from the mobile phone can optionally have a detrimental effect on the body tissue, i.e. not only the radiation transmitted by the transmitter and the antenna, but also the radiation from the remaining components of the mobile phone, such as the microprocessor, the display etc.

The radiation from the transmitter and the antenna of the mobile phone is identical with the radiation used in a microwave oven for heating articles of food, and accordingly it is obvious that such a radiation does have an effect on various types of body tissues. However, the frequencies, the radiation intensities and the radiation length having the detrimental effect are not evident. Tests have shown that a highly intense radiation at specific frequencies can cause cellular changes which in turn can result in for instance development of cancer or fetus deformities. However, such clear indications are only found at relatively strong effects, but assumptions are made that effects at a considerably lower radiation intensity for a long period can result in diseases and damages as well. However, no specific indication has yet been found of the detrimental frequencies, the detrimental radiation levels and the detrimental radiation lengths. However, there is a general agreement that a possible reduction of the radiation level is likely to have a beneficial effect in the long run.

Many devices for shielding against radio radiation and other types of radiation from mobile phones are known. These devices can be classified according to the structure of the shielding.

A first class deals with devices for shielding existing mobile phones. WO 02/095867 A1 describes for instance a number of such devices. One of these devices is in form of a box or a bag in which the mobile phone is placed, and where the box or the bag is made of a material possessing shielding properties, such as a metallic fabric or plate elements. The placing of the mobile phone in such a bag or such a box renders it possible to shield against most of the transmitted electromagnetic radiation. Accessories are also described, such as for instance particularly structured hats or glasses rendering it possible to insert a length of shielding material between the mobile phone and the ear of the user when the mobile phone is used. The latter material must necessarily be penetrable by sound waves. Other publications, such as for instance JP 11-261271, describe how the cover of a mobile phone can be provided with a thin layer shielding against the electromagnetic radiation.

DE 201 03 737 U1 discloses a device made of at least 30% of precious stones, semi-precious stones or crystal, where the device is arranged adjacent a radiation source so as to limit the electromagnetic radiation.

Other devices for reducing the radiation involve means arranged in or about the transmitter of the mobile phone or in and about the antenna of said mobile phone with the result that the radiation from the mobile phone in a specific direction, such as towards the head of the user, differs significantly from the radiation in another direction, such as away from the head of the user. Such devices can for instance be shielding devices of the type described in GB 2350725 A, where said device is arranged between the transmitter of the mobile phone and the side of said mobile phone facing the user during ordinary use. Such devices can be formed by a shield possessing ordinary, shielding properties. Other patents, such as GB 2336035, describe units which are secured to the antenna of a mobile phone, and which change the form of the radiation field about the antenna of the mobile phone in such a manner that the radiation towards the head of the user is reduced.

Finally, according to GB 2350482 A the position of the antenna can be changed relative to the position ordinarily used in connection with mobile phones in such a manner that it is directed away from the user and further such that the field adjacent the head of the user is thereby reduced. Mobile phones are also described where a particular antenna design changes the intensity of the radiated field about the mobile phone.

The above solutions and other solutions of such a nature do more or less change the radiation that the user of a mobile phone is subjected to. The described techniques are, however, encumbered with a number of draw-backs. The main purpose of a mobile phone is indeed that it is portable, i.e. it is so small that it can fit in a bag or a pocket and is light. In addition, it must be possible to use the mobile phone in a way not bending, braking or damaging the shielding equipment. Some solutions place the mobile phone inside a shielding device, and such shielding devices are likely to shield well against the radiation. However, such shielding devices increase the size and the weight of the mobile phone as well and results in a reduced user-friendliness of the mobile phone. Correspondingly, several devices are secured in and about the transmitter or on the antenna, and they do indeed shield the user against radiation, but these devices also make the mobile phone rather unhandy and increase possibly the weight thereof with the result that the user-friendliness of the mobile phone is reduced. It is of vital importance that the properties of the transmitter/receiver in the mobile phone are not changed significantly.

All the above solutions include more or less the so-called conventional shielding means for shielding a mobile phone, i.e. metallic devices of an electrically conducting material and/or a ferromagnetic material known to possess good properties with respect to shielding against radiation. However, yet another possibility exists of shielding for instance mobile phones against radiation.

DISCLOSURE OF INVENTION

The object of the invention is to provide a shielding device of the above type for shielding against electromagnetic radiation from electronic units with a transmitter, such as mobile phones, and which simultaneously is relatively light, compact and reliable and can be included in a simple manner during the design phase of the electronic units or be mounted later on in existing electronic units.

A shielding device of the above type is according to the invention characterised in that it includes a crystal and a winding/spiral, where the winding/spiral is wound about the crystal, and where one end of the winding extends immediately adjacent the antenna of the electronic unit. Such a device operates as a suction circuit and is able to transfer the energy of a transmitted radiation from one location to another location, or in other words it is able to reflect a radiation. The principle of such a device is in many respects identical with the principle of a crystal set, i.e. where the crystal in principle operates as a receiver for the electromagnetic radiation, and where the flat disk-shaped winding intercepts and transfers the energy from the electromagnetic radiation and directs it towards the antenna. Here the advantage is exactly that the crystal, such as for instance rock crystal, snow quartz or rose quartz, possesses shielding properties in connection with electromagnetic radiation, where the electromagnetic radiation is intercepted by the crystal and transferred to the flat disk-shaped winding. In this connection, the crystal possesses some very important properties. The structure and high Q value of the crystal renders it very difficult, i.e. almost impossible in practice to change the oscillating frequency or frequencies of the crystal, and accordingly the inductance and the capacity of the flat disk-shaped winding are of minor importance. In addition, it turned out that the winding direction of the flat, disk-shaped winding as well as the winding direction of one end of the winding about the antenna of the electronic unit are important because one specific winding direction about the crystal and relative to the mobile phone is necessary while one end of the winding must be wound in a specific direction about the antenna. It is often necessary to use "trial and error" in order to determine the correct winding direction because said winding direction depends inter alia on the position and structure of the antenna.

Such a system is unusual compared to the devices ordinarily used in connection with a shielding of for instance mobile phones. However, tests have shown that a rather significant reduction is obtained of the electromagnetic radiation emitted by the mobile phone towards the user without simultaneously significantly deteriorating the transmitting/receiving conditions of the mobile phone, which can be the case of the conventional known techniques.

BRIEF DESCRIPTION OF THE DRAWINGS

The invention is explained in detail below with reference to the drawings, in which.

BEST MODE FOR CARRYING OUT THE INVENTION

Figure 1:
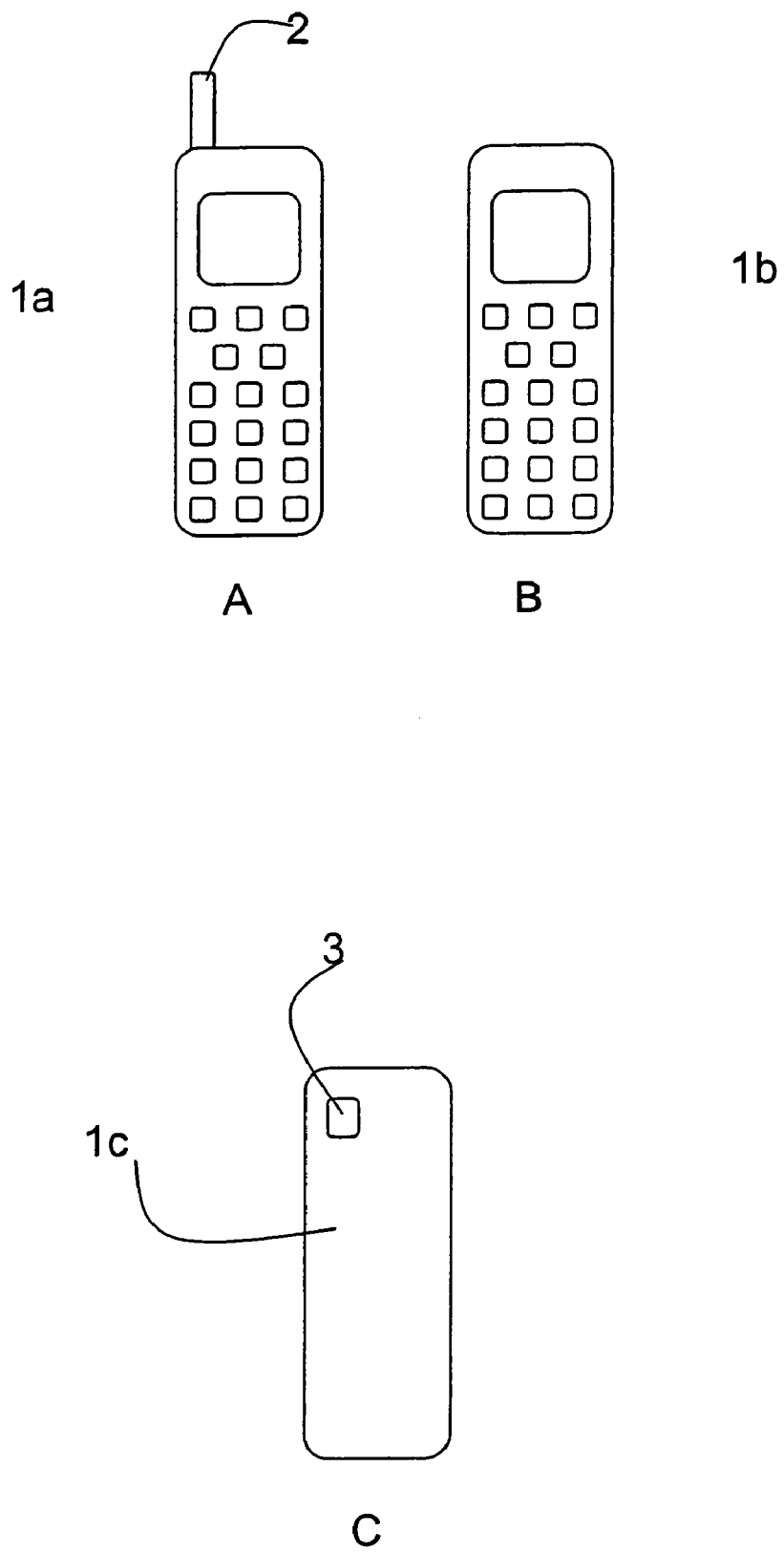
FIGS. 1A to 1C show a mobile phone with an external antenna (a), a mobile phone without such an external antenna (b), and the positioning of a patch-type antenna (c), respectively.

The same reference numerals are used for the same elements.

FIG. 1A shows a mobile phone a with an external antenna 2, and FIG. 1B shows a mobile phone b without an external antenna. These two types of mobile phones are the most frequently used types of mobile phones, and accordingly the description of the invention is focused on these two embodiments. However, the latter should not be understood in a limiting way because the shielding device according to the invention can also be used in connection with other electronic units including a built-in transmitter/receiver. The antenna 2 of the shown mobile phone a is arranged on the left side of the mobile phone, but it can also be arranged on the right side (not shown) of the mobile phone or at another location on the mobile phone, such as on the rear side or the front side, or on the side about the hinge in case the mobile phone is of the folding type. Other types of mobile phones b include an internal antenna, i.e the antenna is not visible on the mobile phone shown in FIG. 1B. The mobile phone b shown in FIG. 1B includes instead a so-called patch-antenna built into the cover of the mobile phone b. The patch-antenna 3 can be arranged at various locations in the mobile phone, but it is often arranged at the uppermost end about the loudspeaker of the mobile phone, cf. FIG. 1C, and as shown it can for instance be arranged in the left side of the mobile phone, but it can also be arranged in the middle or in the right side of said mobile phone. The type of antenna used has no particular effect on how the shielding device according to the invention operates, but as described below the type of antenna has an effect on the positioning of said shielding device.

Figure 2:
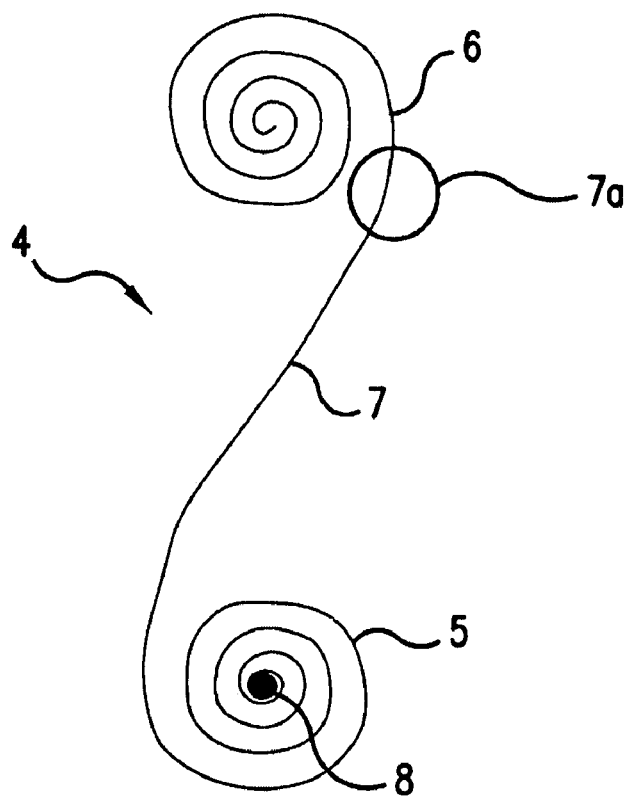
FIG. 2 and 2A show a device according to the invention.
Figure 2A:
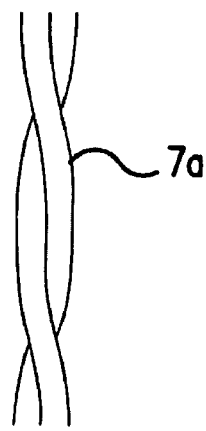

FIG. 2 shows the shielding device according to the invention. The shielding device 4 includes a first winding 5 and a second winding 6 interconnected through a wire 7, where a crystal 8 is arranged at the centre of the first winding 5. The first winding 5 is usually a flat, disk-shaped winding arranged about the crystal 8, and it can include an arbitrary number of windings, such as between 1 and 100 windings. When the first winding 5 is flat and disc-shaped, the wire is usually arranged as a spiral in one layer. However, the winding 5 can include more layers and present a predetermined thickness, which can be advantageous when the shielding device 4 is to be used as a component on a circuit card. The shielding device 4 has much in common with an old-fashioned crystal set where the crystal 8 operates as a receiver for electromagnetic radiation, and where the first winding 5 operates as a receiver and the second winding 6 operates as a transmitter for the electromagnetic radiation received by the crystal 8. As a result, the device operates also as a suction circuit known for instance from radio technology, and accordingly it is able to intercept and transmit electromagnetic radiation. The windings 5, 6 and the connecting wire 7 are made of a material possessing a good conductivity, such as for instance copper, silver, gold or the like materials, and usually the wire can per se be insulated, such as by means of a lacquer or an insulating synthetic material, or it can be bare. The winding can also include two or more wires twisted about one another 7 a, as shown in the magnified section in FIG. 2A. and the individual wires can possess differing, electric properties.

The crystal 8 used can be of many types, both natural and synthetic. Tests have shown that the two natural crystals, snow quartz and rose quarts, are suitable crystals, but other types of crystals with similar properties are also usable. The important feature to be observed when selecting crystals is the properties of the crystals with respect to electromagnetic radiation within the frequencies involved in connection with an electronic unit including a transmitter/receiver.

As mentioned, the first winding 5 operates as a receiver for the electromagnetic radiation received by the crystal 8, and this radiation is transferred to the second winding 6.

Therefore, the second winding 6 can advantageously be arranged in connection with the electronic unit antenna with the result that subsequently the electromagnetic radiation can again be emitted away from the user.

The use of the shielding device 4 according to the invention renders it possible to identify the locations in the mobile phone with the particularly intense radiation. Subsequently the first winding 5 with the crystal 8 is arranged immediately adjacent said location whereafter the second winding 6 is connected to the antenna of the device.

Figure 3:
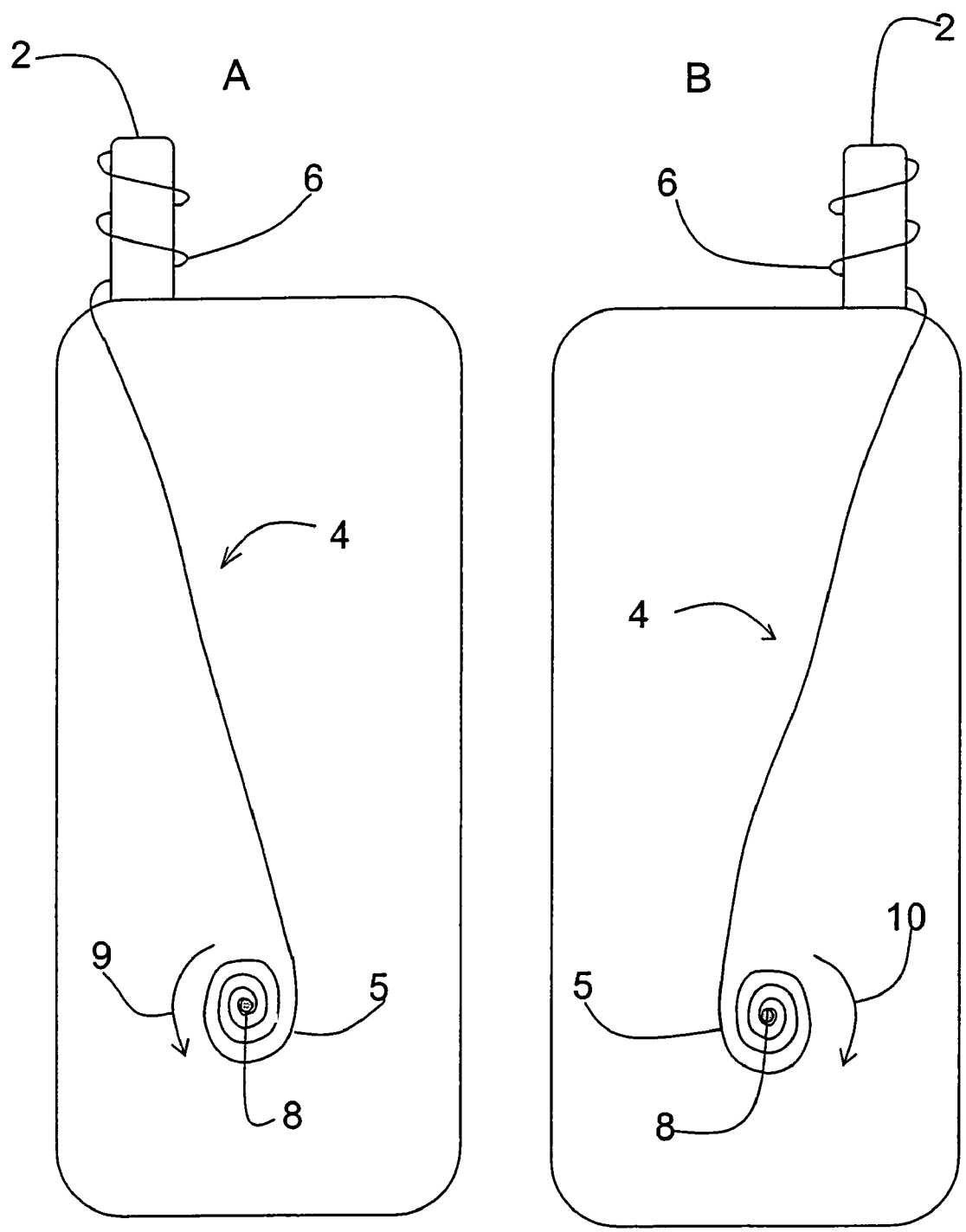
FIGS. 3A and 3B show the position and the winding direction of the windings in a mobile phone with an external antenna.

FIG. 3 shows two examples of how the shielding device 4 according to the invention is arranged in a mobile phone. The two examples show the antenna 2 of the mobile phone arranged to the right and to the left, respectively, on said mobile phone. It turned out that the winding direction of the first winding 5 about the crystal and of the second winding 6 about the antenna 2, respectively, is important because an "incorrect" winding direction results in a deterioration of the shielding effect of the device according to the invention. Tests have shown that the first winding 5 must be wound counterclockwise from the inside and outwards about the crystal 8 and clockwise about the antenna of the mobile phone when the antenna is arranged on the left side of the mobile phone, cf. FIG. 3A. In FIG. 3B the antenna of the mobile phone is arranged on the right side of said mobile phone, and then the first winding 5 must be wound clockwise about the crystal 8 from the inside and outwards and counterclockwise about the antenna 2 of said mobile phone. In addition it turned out that when the winding direction of the first or the second winding 5, 6, respectively, is reversed, then the shielding effect is significantly reduced. However, the latter observation is based on tests by means of "trial and error", and the structure of the antenna per se is likely to determine the winding direction providing the desired shielding. The latter has been tested at laboratories particularly adapted to measure the radiation from mobile phones, and below one possible explanation is given of why this is so.

Figure 4:
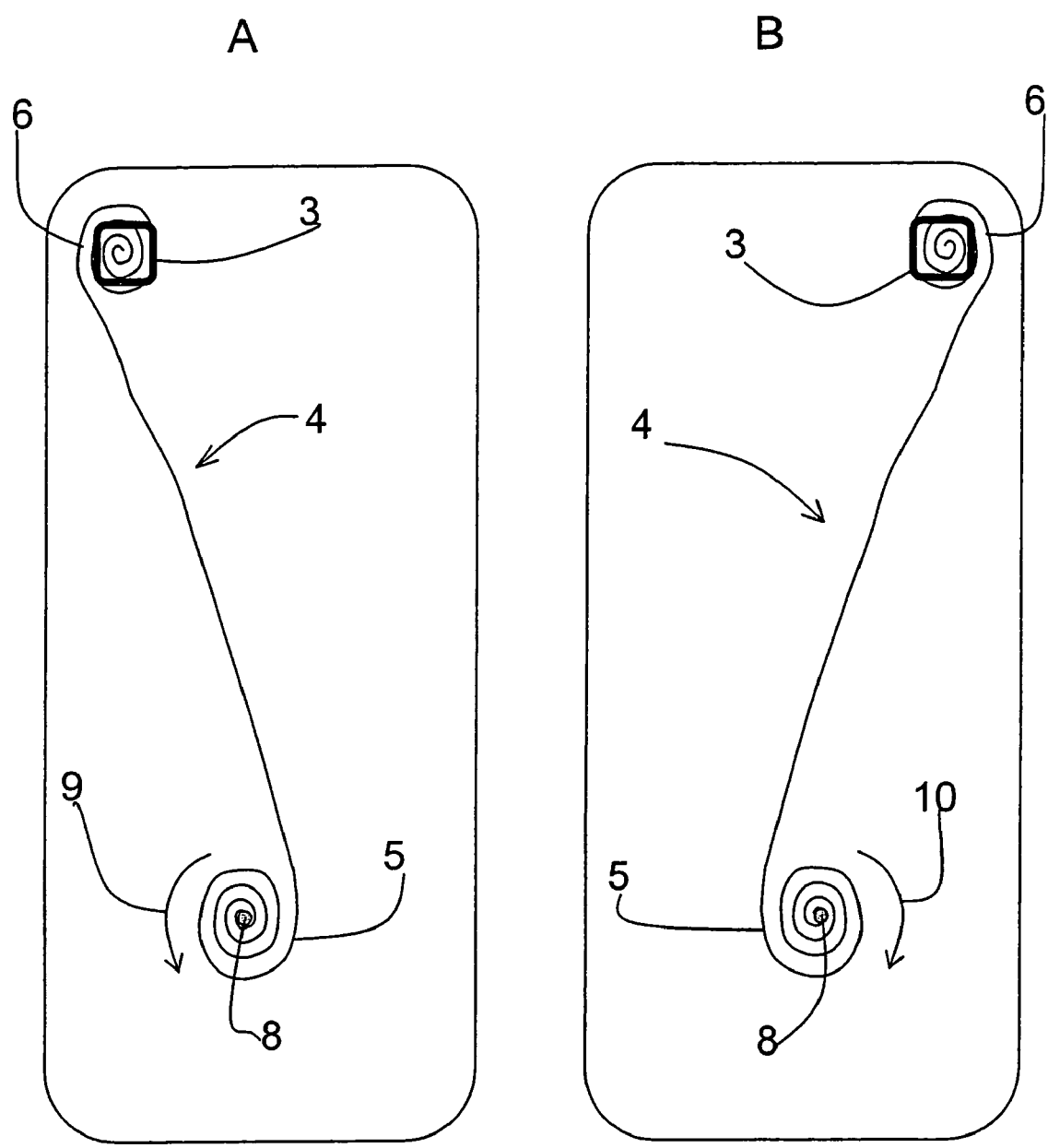
FIGS. 4A and 4B shows the position and the winding direction in the same manner as in FIG. 3, but in an internal antenna.

In the same manner as FIG. 3, FIG. 4 shows the positioning of the shielding device 4 according to the invention, but where an internal patch-type antenna is used. Unlike the external antenna 2, the internal antenna is arranged inside the cover of the mobile hone with the result that the second winding 6 cannot necessarily be wound about the patch-type antenna 3, but is instead arranged as a winding immediately atop/next to the patch-type antenna 3. Tests have shown that the same conditions with respect to winding direction and positioning of the patch-type antenna 3 apply as the conditions applying to the external antenna described in connection with FIG. 3.

As mentioned above, it turned out that the winding direction of the first and the second winding 5, 6 is important because an "incorrect" winding direction results in a significantly poorer shielding effect than the effect obtained by a "correct" winding direction. The latter is probably due to the fact that especially the second winding 6 requires a good coupling to the antenna of the electronic unit. In connection with an external antenna, the choosing of a "correct" or "incorrect" winding direction can imply that a clockwise wound wire in the antenna necessitates that the second winding 6 must also be clockwise wound in order to obtain the best possible coupling between the antenna and the second winding 6. When the opposite winding direction is chosen, a coupling still exists between the antenna 2 and the second winding 6, but this coupling is significantly poorer than the above coupling with the result that the shielding effect is also significantly poorer than the one obtained above. The same applies to a patch-type antenna 3 where the second winding 6 including a clockwise wound patch-type antenna 3 must necessarily also be clockwise wound which results in a large number of possible winding directions in response to the type and position of the antenna, and then some of these winding directions are particularly good and some are particularly poor. As the winding direction used can be difficult to see directly from the outer side of the antenna, it is often necessary to use a so-called "trial and error"-method to determine the possible winding directions of a specific embodiment of the electronic unit.

It should be noted that several shielding devices 4 according to the invention can be used in the same electronic unit for shielding against several separate sources of radiated electromagnetic radiation. Several first windings 5 with crystals 8 must then be arranged at different locations inside the mobile phone in order to obtain a good shielding. Accordingly, the first winding 5 with the crystal 8 can be carried out as a standard component which can be arranged for instance on a circuit card in form of an integrated circuit or another type of component, and where the connection 7 and the second winding 6 are to be connected to a pin on this component.

Figure 5:
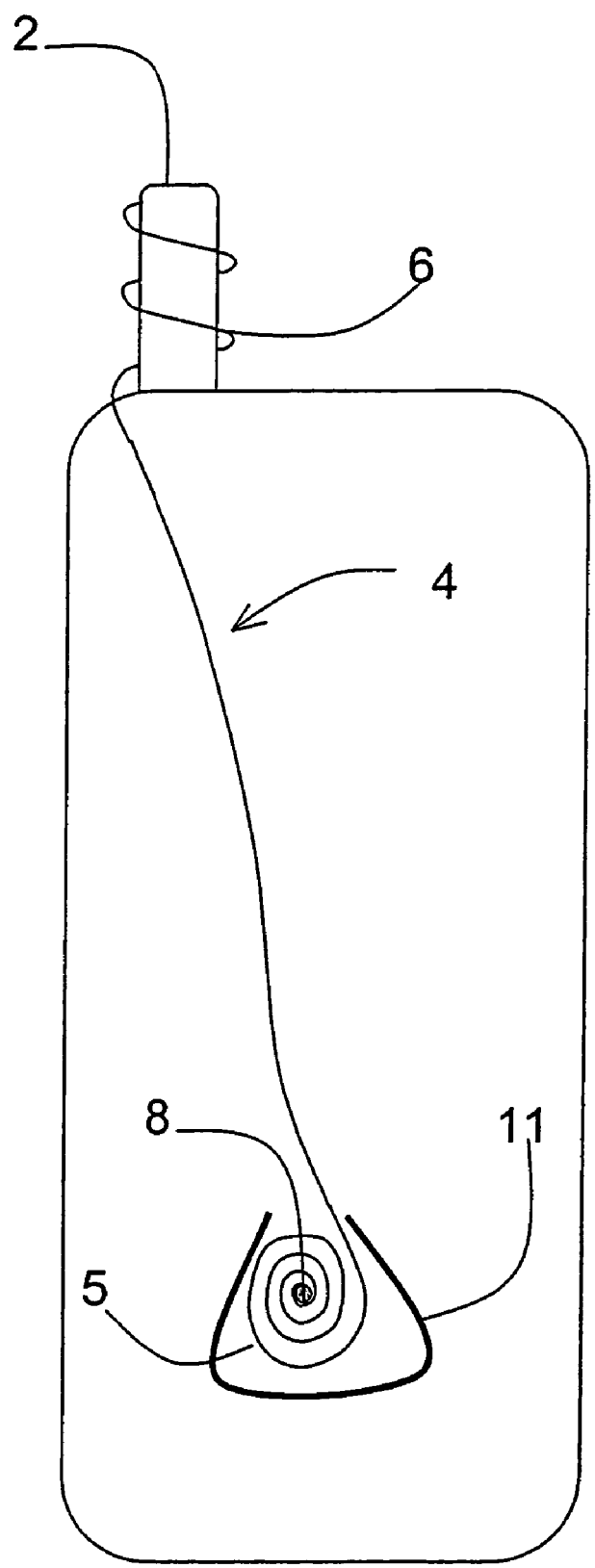
FIG. 5 shows the inclusion of a ferromagnetic element.

It should be noted that FIGS. 3 to 5 may give the impression that the shielding device according to the invention is a post-mounted component used for shielding an existing electronic unit, such as for instance a mobile phone. The shielding device according to the invention can indeed also be used in this manner, but it can also be included during the design phase of for instance a mobile phone with the result that the associated components, viz. the first and the second winding 5, 6 and the crystal 8 are built into the mobile phone in an advantageous manner with respect to the design. In addition, it is not immediately visible that the mobile phone is equipped with such a shielding device.

As illustrated in FIG. 5, the shielding device can also be provided with an additional winding 11 for instance in form of a wire with ferromagnetic properties, i.e. an iron wire or a nickel wire. The shielding device has per se a shielding effect without the above wire, but when the wire is arranged as shown in FIG. 5 about the first winding 5, the shielding effect of the shielding device is significantly improved. This additional winding can include a single, open winding as shown in FIG. 5 or several open windings. Tests have surprisingly shown that when the additional winding 11 is formed as a polygon, and in particular as an open triangle as shown in FIG. 5, then it ensures a particularly good shielding effect. The wire 11 with the ferromagnetic properties can be made of several different materials, such as for instance ordinary iron wire, but it can also include materials, such as other ordinary ferromagnetic materials or more exotic ferromagnetic materials, such as permaloy or µ-metal. Tests have also shown that an additional winding 11 must not intersect the wire of the first and the second winding 5, 6 as the shielding effect is then reduced.

The device can also include a metallic film arranged adjacent the antenna 2 of the device and between said antenna and the user. The film is made of a material with a good electric conductivity, such as aluminium, copper, silver, gold or other metals and alloys with a good electric conductivity. The film is not intended to surround the antenna 2, but it is to operate as a mirror for the radiation from the antenna. The film can also include a bright and a mat side where the bright side is to turn away from the user. Tests have shown that a mobile phone including such a film can provide a further shield for the user.

The invention relates also to a method of arranging a shielding device according to the invention. The method renders it possible to identify locations on/in for instance a mobile phone where the electromagnetic radiation is particularly intense/problematic, and where the shielding device according to the invention is arranged immediately adjacent said location with the result that said radiation is transferred to the antenna through the wire 7 connected to the second winding 6. As a result it is possible to shield against not only a single source of electromagnetic radiation, but also against several sources of electromagnetic radiation from the said unit.

The invention has been described with reference to some embodiments. The scope of the invention is indicated in the following claims, but it is not to be considered limited to said claims, and many alterations and modifications can be carried out without thereby deviating from the object of the invention.

The invention claimed is:

1. A device for shielding an electronic unit against electromagnetic radiation, the electronic unit including a transmitter with an antenna, the device comprising:
   a crystal; and
   a first electrically conductive wire having a first winding wound around the crystal at a first end, and a second winding wound around the antenna of the electronic unit at the opposite end, wherein
   the first and second windings each include at least two loops, said first winding receiving electromagnetic radiation which is then emitted away from said device by said second winding.

2. A device according to claim 1 wherein the first winding is spiral, flat, and disk-shaped.

3. A device according to claim 1, wherein the first electrically conductive wire is formed by two or more wires twisted about one another.

4. A device according to claim 1, wherein the first winding is wound counterclockwise about the crystal from the inside and outwards, and the second winding is wound clockwise about the antenna when the antenna of the electronic unit is an external antenna arranged on the left side of said electronic unit.

5. A device according to claim 1, wherein the first winding is wound clockwise about the crystal from the inside and outwards, and the second winding is wound counterclockwise about the antenna when said antenna is an external antenna arranged on the right side of the electronic unit.

6. A shielding device for an electric unit against electromagnetic radiation, the electronic unit including transmitter and receiving equipment and an antenna comprising a crystal and a winding formed by electrically conductive wire, the device comprising:
   a first and a second, flat and disc-shaped winding, arranged as spirals and interconnected through an electrically conductive wire wherein:
   the first winding is wound about the crystal in a direction determined by the position of the antenna, and placed at a position with intense electromagnetic radiation in the electronic unit; and
   the second winding is wound about the antenna, such that said second winding direction is opposite the first winding direction, so that the shielding device operates as a suction circuit wherein the first winding with the crystal acts as a receiver for the electromagnetic radiation which is transferred to the second winding with the antenna where it is emitted away from said device.

7. A device according to claim 6, wherein the electrically conductive wire formed by two or more wires twisted about one another.

8. A device according to claim 6, wherein the first winding is comprised of an electrically conductive wire formed by two or more wires twisted about one another.

9. A device according to claim 6, wherein the second winding is comprised of an electrically conductive wire formed by two or more wires twisted about one another.

* * * * *